US007157413B2

(12) United States Patent
Lazzeri et al.

(10) Patent No.: US 7,157,413 B2
(45) Date of Patent: Jan. 2, 2007

(54) DETERGENT COSMETIC COMPOSITIONS COMPRISING AN ANIONIC SURFACTANT, AN AMPHOTERIC, CATIONIC, AND/OR NONIONIC SURFACTANT, AND A POLYSACCHARDIE, AND USE THEREOF

(75) Inventors: Pascale Lazzeri, Levallois-Perret (FR); Alice Aprville, Levallois-Perret (FR)

(73) Assignee: L'Oreal, Paris (FR)

( * ) Notice: Subject to any disclaimer, the term of this patent is extended or adjusted under 35 U.S.C. 154(b) by 206 days.

(21) Appl. No.: 10/614,092

(22) Filed: Jul. 8, 2003

(65) Prior Publication Data

Related U.S. Application Data

(60) Provisional application No. 60/407,708, filed on Sep. 4, 2002.

(30) Foreign Application Priority Data

Jul. 8, 2002 (FR) .................................. 02 08553

(51) Int. Cl.
C11D 1/02 (2006.01)
C11D 1/86 (2006.01)
C11D 3/22 (2006.01)
A61K 8/73 (2006.01)

(52) U.S. Cl. ...................... 510/119; 510/121; 510/122; 510/125; 510/127; 510/151; 510/155; 510/470; 424/401; 424/70.12; 424/70.13; 424/70.19; 424/70.21; 424/70.22

(58) Field of Classification Search ................ 510/119, 510/121, 122, 125, 127, 151, 155, 470; 424/401, 424/70.12, 70.13, 70.19, 70.21, 70.22
See application file for complete search history.

(56) References Cited

U.S. PATENT DOCUMENTS

| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,528,378 | A | 10/1950 | Mannheimer |
| 2,781,354 | A | 2/1957 | Mannheimer |
| 2,961,347 | A | 11/1960 | Floyd |
| 3,206,462 | A | 9/1965 | McCarty |
| 3,227,615 | A | 1/1966 | Korden |
| 3,472,840 | A | 10/1969 | Stone et al. |
| 3,632,559 | A | 1/1972 | Matter et al. |
| 3,874,870 | A | 4/1975 | Green et al. |
| 3,912,808 | A | 10/1975 | Sokol |
| 3,917,817 | A | 11/1975 | Vanlerberghe et al. |
| 3,929,990 | A | 12/1975 | Green et al. |
| 3,966,904 | A | 6/1976 | Green et al. |
| 3,986,825 | A | 10/1976 | Sokol |
| 4,001,432 | A | 1/1977 | Green et al. |
| 4,005,193 | A | 1/1977 | Green et al. |
| 4,013,787 | A | 3/1977 | Varlerberghe et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,031,307 | A | 6/1977 | DeMartino et al. |
| 4,075,136 | A | 2/1978 | Schaper |
| 4,131,576 | A | 12/1978 | Iovine et al. |
| 4,166,894 | A | 9/1979 | Schaper |
| 4,172,887 | A | 10/1979 | Vanlerberghe et al. |
| 4,223,009 | A | 9/1980 | Chakrabarti |
| 4,240,450 | A | 12/1980 | Grollier et al. |
| 4,277,581 | A | 7/1981 | Vanlerberghe et al. |
| 4,349,532 | A | 9/1982 | Vanlerberghe et al. |
| 4,381,919 | A | 5/1983 | Jacquet et al. |
| 4,591,610 | A | 5/1986 | Grollier |
| 4,693,935 | A | 9/1987 | Mazurek |
| 4,728,571 | A | 3/1988 | Clemens et al. |
| 4,761,273 | A | 8/1988 | Grollier et al. |
| 4,839,166 | A | 6/1989 | Grollier et al. |
| 4,957,732 | A | 9/1990 | Grollier et al. |
| 4,972,037 | A | 11/1990 | Garbe et al. |
| 4,996,059 | A | 2/1991 | Grollier et al. |
| 5,089,252 | A | 2/1992 | Grollier et al. |
| 5,196,189 | A | 3/1993 | Jacquet et al. |
| 5,773,611 | A | 6/1998 | Zysman et al. |
| 6,210,691 | B1 | 4/2001 | Mahieu et al. |
| 6,696,067 | B1 * | 2/2004 | Brandt et al. ............... 424/401 |

FOREIGN PATENT DOCUMENTS

| DE | 44 02 929 C1 | 6/1995 |
| DE | 44 20 736 C1 | 8/1995 |

(Continued)

OTHER PUBLICATIONS

English language Derwent Abstract of FR 2 795 951, Jan. 12, 2001.

(Continued)

Primary Examiner—Brian P Mruk
(74) Attorney, Agent, or Firm—Finnegan, Henderson, Farabow, Garrett & Dunner, LLP

(57) ABSTRACT

Novel compositions such as detergent and conditioning cosmetic compositions, comprising, in a cosmetically acceptable medium, at least one anionic surfactant, at least one other surfactant chosen from amphoteric, nonionic and cationic surfactants and at least one polysaccharide chosen from starch hydrolyzates and nonionic and anionic fructans, as well as their use for cleaning and caring for the hair.

63 Claims, No Drawings

FOREIGN PATENT DOCUMENTS

| | | |
|---|---|---|
| DE | 44 24 530 A1 | 1/1996 |
| DE | 44 24 533 A1 | 1/1996 |
| EP | 0 080 976 B1 | 6/1983 |
| EP | 0 122 324 | 10/1984 |
| EP | 0 186 507 A2 | 7/1986 |
| EP | 0 227 994 B1 | 7/1989 |
| EP | 0 337 354 | 10/1989 |
| EP | 0 342 834 B1 | 11/1989 |
| EP | 0 412 704 B1 | 2/1991 |
| EP | 0 412 707 B1 | 2/1991 |
| EP | 0 582 152 B1 | 2/1994 |
| EP | 0 646 572 B1 | 4/1995 |
| FR | 1 492 597 | 9/1966 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 589 476 | 5/1987 |
| FR | 2 598 611 | 11/1987 |
| FR | 2 673 179 | 8/1992 |
| FR | 2 795 951 | 1/2001 |
| FR | 2 795 953 | 1/2001 |
| FR | 2795953 * | 1/2001 |
| GB | 1546809 | 5/1979 |
| WO | WO 95/23807 | 9/1975 |
| WO | WO 93/23009 | 11/1993 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/16665 | 6/1995 |
| WO | WO 95/21181 | 8/1995 |
| WO | WO 95/34531 | 12/1995 |
| WO | WO 96/01799 | 1/1996 |
| WO | WO 96/01807 | 1/1996 |

OTHER PUBLICATIONS

English language Derwent Abstract of FR 2 795 953, Jan. 12, 2001.
Certified English language translation of FR 2,795,953, cited by Examiner in Office Action mailed May, 4, 2005.
Derwent Abstract for EP 0 080 976.
Derwent Abstract for FR 2 589 476.
Porter, M.R., *Handbook of Surfactants*, Blackie: Glaskow and London, 1991, pp. 116-178.

* cited by examiner

DETERGENT COSMETIC COMPOSITIONS COMPRISING AN ANIONIC SURFACTANT, AN AMPHOTERIC, CATIONIC, AND/OR NONIONIC SURFACTANT, AND A POLYSACCHARDIE, AND USE THEREOF

This application claims benefit of U.S. Provisional Application No. 60/407,708, filed Sep. 4, 2002.

Disclosed herein are novel cosmetic compositions with improved properties, which are intended for both cleaning and conditioning keratin materials, such as the hair, and comprising, in a cosmetically acceptable support, at least one anionic surfactant, at least one other surfactant chosen from amphoteric, nonionic and cationic surfactants, and at least one polysaccharide chosen from starch hydrolyzates and nonionic and anionic fructans.

Further disclosed herein is the use of said compositions in the above-mentioned cosmetic application.

It is common practice to use detergent hair compositions, or shampoos based essentially on standard anionic, nonionic and/or amphoteric surfactants, for example, anionic surfactants, to clean and/or wash the hair. These compositions may be applied to wet hair and the lather can be generated by massaging or rubbing with the hands. The massaging or rubbing can remove, after rinsing with water, the various types of soiling which may initially be present on the hair.

Admittedly, these base compositions can have good washing power, but the intrinsic cosmetic properties associated with them can nevertheless remain fairly poor, owing, for example, to the fact that the relatively aggressive nature of such a cleaning treatment can, in the long run, lead to more or less pronounced damage to the hair fiber. This damage can be associated, for example, with the gradual removal of the lipids or proteins contained in or on the surface of this fiber.

Thus, in order to improve the cosmetic properties of the above detergent compositions, such as those intended to be applied to sensitized hair (i.e., hair which has been damaged or made brittle, for example, under the chemical action of atmospheric agents and/or hair treatments such as permanent-waving, dyeing or bleaching), it is now common to introduce additional cosmetic agents known as conditioners into these compositions, wherein these conditioners may, for example, repair or limit the harmful-or undesirable effects induced by the various treatments or aggressions to which the hair fibers may be subjected more or less repeatedly. These conditioners may, of course, also improve the cosmetic behavior of natural hair.

The conditioners most commonly used to date in shampoos are, for example, cationic polymers, silicones and/or silicone derivatives, which may give washed, dry or wet hair an ease of disentangling and a softness which may be markedly better than that which can be obtained with corresponding cleaning compositions from which they are absent.

However, the cosmetic advantages mentioned above may unfortunately also be accompanied, on dried hair, by certain cosmetic effects that may be considered undesirable, for example, lankness of the hairstyle and a lack of smoothness.

In addition, the use of cationic polymers for this purpose can have at least one drawback. On account of their high affinity for the hair, some of these polymers can become deposited on the hair in a substantial amount during repeated use, and may lead to at least one of the following undesirable effects: unpleasant, laden feel, stiffening of the hair and adhesion between the fibers, which may affect the styling. These drawbacks may be accentuated in the case of fine hair, which can lack liveliness and volume.

In summary, it is found that the current cosmetic compositions comprising conditioners may not be entirely satisfactory.

On sensitized hair, in order to obtain the cosmetic effects of silicones over the entire length of the hair fiber, combinations of silicones and of cationic polymers may, for example, be used.

However, and despite the progress recently made in the field of shampoos based on cationic polymers and silicones, these shampoos may not really be entirely satisfactory, and as such there is currently still a strong need for novel products that show improved performance in respect to at least one of the cosmetic properties mentioned above.

Disclosed herein are compositions directed toward satisfying such a need.

Thus, after considerable research conducted in this matter, the inventors have now found, entirely surprisingly and unexpectedly, that by using a particular washing base, for example, a washing base comprising at least one anionic surfactant and at least one other surfactant chosen from amphoteric, nonionic and cationic surfactants in a particular ratio, and further comprising at least one particular polysaccharide, it may be possible to obtain detergent compositions that show at least one excellent cosmetic property, for example, ease of styling, hold, liveliness, smoothness and disentangling of treated hair, and also very good intrinsic washing power. Moreover, the hair may not be laden, and may have a natural and clean feel.

All these discoveries form the basis of the compositions disclosed herein. Thus, novel compositions disclosed herein, for example, detergent and conditioning hair compositions, are now proposed, comprising, in a cosmetically acceptable medium, at least one anionic surfactant, at least one other surfactant chosen from amphoteric, nonionic and cationic surfactants, and at least one polysaccharide chosen from starch hydrolyzates with a dextrose equivalent (DE) of less than 20 and from nonionic and anionic fructans, wherein the weight ratio of the at least one anionic surfactant to the at least one other surfactant is greater than or equal to 1:1.

For example, said at least one polysaccharide is-soluble in the composition. Further, for example, said at least one polysaccharide is water-soluble.

Starch hydrolyzates are known (see Encyclopedia of Chemical Technology by Kirk-Othmer, 3rd ed., Vol. 22, 1978, pp. 499 to 521) and may be classified, according to their dextrose content, on the one hand as starch syrups, and on the other hand as maltodextrins.

Starch syrups are starch hydrolyzates with a dextrose equivalent (DE) of greater than 20, and maltodextrins are starch hydrolyzates with a DE of less than 20. The DE is the number of grams of reducing sugars (considered as dextrose) per 100 g of product dry matter. The DE thus measures the degree of hydrolysis of the starch, because, the more the product comprises small molecules (such as dextrose and maltose), the higher its DE. In contrast, the more the product comprises large molecules (polysaccharides), the lower its DE.

Starch syrups (DE>20) and maltodextrins are known in the field: of haircare as being useful in preparing hair fixing compositions.

Starch syrups (DE>20),used at concentrations of greater than 10% by weight are moreover described to improve the foam quality of shampoo compositions.

Disclosed herein is also the cosmetic use of the compositions described above for cleaning and conditioning the hair.

However, other characteristics, aspects and advantages of the compositions; disclosed herein will emerge even more clearly on reading the description that follows and also the concrete, but in no way limiting, examples intended to illustrate it.

As used herein, the term "conditioner" means any agent whose function is to improve at least one cosmetic property of the hair, for example, softness, disentangling, feel and static electricity.

As used herein, the term "nonionic fructan" means a fructan that does not comprise any ionic or ionizable groups such as, for example, primary, secondary or tertiary amines or quaternary ammoniums.

As used herein, the expression "polysaccharide that is soluble in the composition or water-soluble" means polysaccharides having a structure according to the embodiments disclosed, herein, which are soluble in water or in the composition to a concentration of greater than or equal to 0.1% by weight in water at about 25° C., i.e., they form under these conditions a macroscopically isotropic transparent solution.

Should the composition comprise agents other than the at least one polysaccharide, for example, insoluble agents such as insoluble conditioners or nacreous agents, the solubility of the polysaccharides in the composition can be determined in the absence of these insoluble agents.

(i) Anionic Surfactant(s):

In the context of the embodiments disclosed herein, the nature of the at least one anionic surfactant does not represent a truly critical factor.

For example, the at least one anionic surfactant which can be used in the compositions disclosed herein, may be chosen from salts, for example, alkaline salts, such as sodium salts; ammonium salts; amine salts; amino alcohol salts; and magnesium salts of the following compounds: alkyl sulfates, alkyl ether sulfates, alkylamido ether sulfates, alkyl arylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, wherein the alkyl and acyl radicals of all of these various compounds, for example, comprise from 12 to 20 carbon atoms, and the aryl radical may be chosen, for example, from phenyl and benzyl radicals.

The at least one anionic surfactant may, for example, be chosen from fatty acid salts such as the salts of oleic, ricinoleic, palmitic and stearic acids, coconut oil acid and hydrogenated coconut oil acid; acyl lactylates wherein the acyl radical comprises from 8 to 20 carbon atoms. At least one weakly anionic surfactant can also, for example, be used, such as, for example, at least one weakly anionic surfactant chosen from alkyl-D-galactosiduronic acids and the salts thereof, as well as polyoxyalkylenated ether carboxylic acids and the salts thereof, for example, those comprising from 2 to 50 ethylene oxide groups.

At least one anionic surfactant chosen from polyoxyalkylenated carboxylic ether acid and salt type surfactants may, for example, be used, such as those which correspond to formula (I) below:

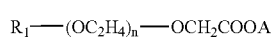  (I)

wherein:
- $R_1$ is chosen from alkyl and alkylaryl groups,
- n is an integer or decimal (average value) ranging from 2 to 24, for example, from 3 to 10, the alkyl radical comprising from 6 to 20 carbon atoms, and the aryl group is, for example, a phenyl group,
- A is chosen from H, ammonium, Na, K, Li, Mg and monoethanolamine and triethanolamine residues. Mixtures of compounds of formula (I) can, for example, also be used, for example, mixtures wherein the groups $R_1$ are different.

At least one anionic surfactant chosen from salts of alkyl sulfates and alkyl ether sulfates may, for example, be used.

(ii) Amphoteric Surfactant(s):

The amphoteric surfactants, whose nature is not a critical feature in the embodiments disclosed herein, can be, for example, chosen from aliphatic secondary and tertiary amine derivatives wherein the aliphatic radical is chosen from linear and branched chains comprising from 8 to 22 carbon atoms and comprising at least one water-soluble anionic group, for example, at least one one water-soluble anionic group chosen from carboxylate, sulfonate, sulfate, phosphate and phosphonate groups. The amphoteric surfactants may be chosen, further, for example, from $(C_8-C_{20})$ alkylbetaines, sulfobetaines, $(C_8-C_{20})$alkylamido$(C_1-C_6)$ alkylbetaines and $(C_8-C_{20})$alkylamido$(C_1-C_6)$ alkylsulfobetaines, For example, among the amine derivatives, mention may be made of the products sold under the name MIRANOL, as described in U.S. Pat. Nos. 2,528,378 and 2,781,354 and having the structures:

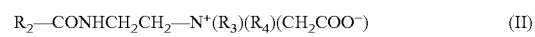  (II)

wherein:
- $R_2$ is chosen from heptyl, nonyl and undecyl radicals, and alkyl radicals derived from an acid $R_2$—COOH present in hydrolyzed coconut oil,
- $R_3$ is a β-hydroxyethyl group, and
- $R_4$ is chosen from carboxymethyl groups;

and

  (III)

wherein:
- B is chosen from —$CH_2CH_2OX'$ groups,
- C is chosen from —$(CH_2)_z$—Y' radicals, wherein z=1 or 2,
- X' is chosen from a —$CH_2CH_2$—COOH radical and a hydrogen atom,
- Y' is chosen from —COOH and —$CH_2$—CHOH—$SO_3H$ radicals,
- $R_5$ is chosen from alkyl radicals of an $R_9$—COOH acid present in coconut oil and in hydrolyzed linseed oil, and alkyl radicals, for example, $C_7$, $C_9$, $C_{11}$ and $C_{13}$ alkyl radicals, a $C_{17}$ alkyl radical and its iso form, and an unsaturated $C_{17}$ alkyl radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

For example, the cocoamphodiacetate sold under the trade name MIRANOL C2M concentrate by the company Rhodia Chimie may be used in the compositions disclosed herein.

(iii) Nonionic Surfactant(s):

The nonionic surfactants may, for example, be chosen from those compounds that are well known per se (see, for example, "Handbook of Surfactants" by M. R. Porter, published by Blackie & Son (Glasgow and London), 1991, pp. 116–178) and, in the embodiments disclosed herein, their nature is not a critical feature. Thus, the nonionic surfactants can be chosen, for example, from polyethoxylated, polypropoxylated and polyglycerolated fatty acids, alkylphenols, α-diols and alcohols comprising at least one fatty chain comprising, for example, from 8 to 18 carbon atoms, it being possible for the number of ethylene oxide or propylene oxide groups to range, for example, from 2 to 50 and for the number of glycerol groups to range, for example, from 2 to 30.

The non-ionic surfactants may also, for example, be chosen from copolymers of ethylene oxide and of propylene oxide, condensates of ethylene oxide and of propylene oxide with fatty alcohols; polyethoxylated fatty amides, for example, those comprising from 2 to 30 mol of ethylene oxide, polyglycerolated fatty amides comprising on average from 1 to 5 glycerol groups, for example, from 1.5 to 4, glycerol groups; polyethoxylated fatty amines, for example, comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$–$C_{14}$) alkylamine oxides and N-acylaminopropylmorpholine oxides.

The non-ionic surfactants may also, for example, be chosen from alkylpolyglycosides for use in the compositions disclosed herein.

(iv) Cationic Surfactants:

The cationic surfactants may, for example, be chosen from:

A) quaternary ammonium salts of general formula (IV) below,

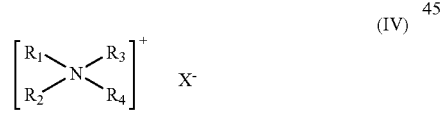

(IV)

wherein:

X⁻ is an anion chosen from halides, such as chloride, bromide and iodide; and ($C_2$–$C_6$)alkyl sulfates, such as methyl sulfate; phosphates; alkyl and alkylaryl sulfonates and anions derived from organic acids, such as acetate and lactate, and (i) —$R_1$ to $R_3$, which may be identical or different, are each chosen from linear and branched aliphatic radicals comprising from 1 to 4 carbon atoms and aromatic radicals such as aryl and alkylarylradicals. The aliphatic radicals can comprise at-least one hetero atom chosen from, for example, oxygen, nitrogen, sulfur, and halogen atoms, and may, for example, be chosen from alkyl alkoxy and alkylamide radicals, and $R_4$ is chosen from linear and branched alkyl radicals comprising from 16 to 30 carbon atoms.

Such cationic surfactants may, for example, be a cetyltrimethylammonium salt, for example, a cetyltrimethylammonium chloride.

ii) —$R_1$ and $R_2$, which may be identical or different, are each chosen from linear and branched aliphatic radicals comprising from 1 to 4 carbon atoms, and aromatic radicals such as aryl and alkylary radicals. The aliphatic radicals can comprise at least one hetero atom, chosen from, for example, oxygen, nitrogen, sulfur and halogen atoms, and are chosen, for example, from alkyl, alkoxy, alkylamide and hydroxyalkyl radicals comprising from 1 to 4 carbon atoms; and $R_3$ and $R_4$, which may be identical or different, are each chosen from linear and branched alkyl radicals comprising from 12 to 30 carbon atoms, wherein the alkyl radicals comprise at least one functional group chosen from ester and amide functional groups; for example, $R_3$ and $R_4$ may each be chosen from ($C_{12}$–$C_{22}$)alkylamido($C_2$–$C_6$)alkyl and ($C_{12}$–$C_{22}$)alkylacetate radicals.

Such cationic surfactants may, for example, be a stearamidopropyldimethyl(myristyl acetate)ammonium salt, for example, stearamidopropyldimethyl(myristyl acetate)ammonium chloride.

B) quaternary ammonium salts of imidazolinium, such as, those of formula (V) below:

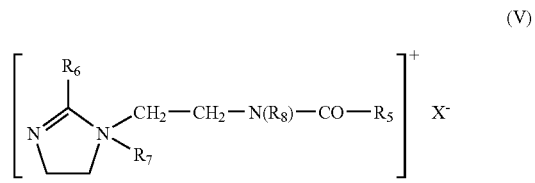

(V)

wherein:

$R_5$ is chosen from alkenyl and alkyl radicals comprising from 8 to 30 carbon atoms, for example, fatty acid derivatives of tallow, $R_6$ is chosen from a hydrogen atom, $C_1$–$C_4$ alkyl radicals, and alkenyl and alkyl radicals comprising from 8 to 30 carbon atoms, $R_7$ is chosen from $C_1$–$C_4$ alkyl radicals, $R_8$ is chosen from a hydrogen atom and $C_1$–$C_4$ alkyl radicals, and X⁻ is an anion chosen from halides, phosphates, acetates, lactates, alkyl sulfates, alkyl sulfonates and alkylaryl sulfonates.

$R_5$ and $R_6$ may, for example, be a mixture of radicals chosen from alkenyl and alkyl radicals comprising from 12 to 21 carbon atoms, such as fatty acid derivatives of tallow, $R_7$ may be a methyl radical and $R_8$ may be a hydrogen atom. Such a product is, for example, Quaternium-27 (CTFA 1997) or Quaternium-83 (CTFA 1997), which are sold under the names "REWOQUAT" W75, W90, W75PG and W75HPG by the company Witco, C) Diquaternary Ammonium Salts of Formula (VI):

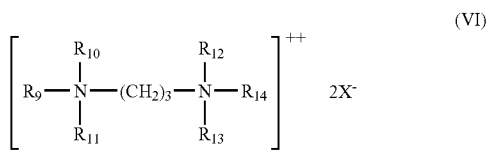

wherein:
R$_9$ is chosen from aliphatic radicals comprising from 16 to 30 carbon atoms,
R$_{10}$, R$_{11}$, R$_{12}$, R$_{13}$ and R$_{14}$, which may be identical or different, are each chosen from hydrogen and alkyl radicals comprising from 1 to 4 carbon atoms, and
X$^-$ is an anion chosen from halides, acetates, phosphates, nitrates and methyl sulfates.

Such diquaternary ammonium salts, for example, include propanetallowdiammonium dichloride; and D) Quaternary Ammonium salts comprising at least one ester functional group of formula (VII) Below:

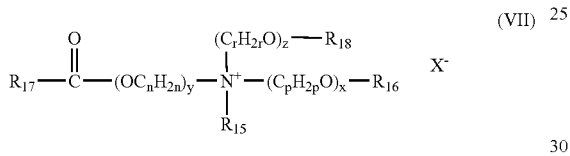

wherein:
R$_{15}$ is chosen from C$_1$–C$_6$ alkyl radicals and C$_1$–C$_6$ hydroxyalkyl and dihydroxyalkyl radicals;
R$_{16}$ is chosen from:
a radical

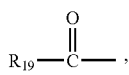

linear and branched, saturated and unsaturated C$_1$–C$_{22}$ hydrocarbon-based radicals R$_{20}$, and a hydrogen atom,
R$_{18}$ is chosen from:
a radical

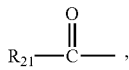

linear and branched, saturated and unsaturated C$_1$–C$_6$ hydrocarbon-based radicals R$_{22}$, and a hydrogen atom,
R$_{17}$, R$_{19}$ and R$_{21}$, which may be identical or different, are each chosen from linear and branched, saturated and unsaturated C$_7$–C$_{21}$ hydrocarbon-based radicals;
n, p and r, which may be identical or different, are each integers ranging from 2 to 6;
y is an integer ranging from 1 to 10;
x and z, which may be identical or different, are integers ranging from 0 to 10;
X$^-$ is chosen from simple and complex organic and inorganic anions; and with the provisos that the sum x+y+z is from 1 to 15, that when x is 0, then R$_{16}$ is R$_{20}$ and that when z is 0, then R$_{18}$ is R$_{22}$.

For example, the compositions disclosed herein may contain ammonium salts of formula (VII) wherein:
R$_{15}$ is chosen from methyl and ethyl radicals,
x and y are equal to 1;
z is equal to 0 or 1;
n, p and r are equal to 2;
R$_{16}$ is chosen from:
a radical

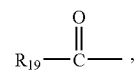

methyl and C$_{14}$–C$_{22}$ hydrocarbon-based radicals, and a hydrogen atom;
R$_{17}$, R$_{19}$ and R$_{21}$, which may be identical or different, are each chosen from linear and branched, saturated and unsaturated C$_7$–C$_{21}$ hydrocarbon-based radicals; and
R$_{18}$ is chosen from:
a radical

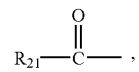

and a hydrogen atom.

Such compounds are sold, for example, under the names DEHYQUART by the company Cognis, STEPANQUAT by the company Stepan, NOXAMIUM by the company Ceca, and REWOQUAT WE 18 by the company Rewo-Witco.

The quaternary ammonium salts may, for example, be chosen from cetyltrimethylammonium chloride and palmitamidopropyltrimethylammonium chloride sold under the name VARISOFT PA TC by, the company Goldschmidt.

The anionic surfactants used in the compositions disclosed herein may, for example, be chosen from at least one of (C$_{12}$–C$_{14}$)alkyl sulfates of sodium, of triethanolamine and of ammonium, the (C$_{12}$–C$_{14}$)alkyl ether sulfates of sodium, of triethanolamine and of ammonium oxyethylenated with 2.2 mol of ethylene oxide, from (C$_{12}$–C$_{14}$)alkylamido sulfates of sodium, of triethanolamine and of ammonium, sodium cocoyl isethionate and sodium (C$_{14}$–C$_{16}$)-α-olefin sulfonate, with:
either an amphoteric surfactant such as the amine derivatives known as disodium cocoamphodipropionate or sodium cocoamphopropionate, sold, for example, by the company Rhodia Chimie under the trade name "MIRANOL C2M Conc." as an aqueous solution comprising 38% active material, or under the name "MIRANOL C32;"
or an amphoteric surfactant of zwitterionic type, such as alkylamidobetaines and alkylbetaines, for example, the cocobetaine sold under the name "DEHYTON AB 30" as an aqueous solution containing 32% AM by the company Cognis, or such as (C$_8$–C$_{20}$)alkylamido (C$_1$–C$_6$)alkylbetaines, for example, Tegobetaine® F 50 sold by the company Goldschmidt.

As a guide, the surfactants used in the compositions disclosed herein may, for example, have the following compositions:

(i) at least one anionic surfactant: from 2% to 50% by weight, relative to the total weight of the composition, for example, from 3% to 30% by weight, relative to the total weight of the composition, and even further, for example, from 3% to 20% by weight, relative to the total weight of the composition;

(ii) at least one other surfactant chosen from amphoteric, nonionic and cationic surfactants: from 1% to 50% by weight, relative to the total weight of the compostion, for example, from 1% to 20% by weight, relative to the total weight of the composition, and even further, for example, from 1% to 10% by, weight, relative to the total weight of the composition.

The total amount of the surfactants described above may, for example, be greater than or equal to 4% by weight, relative to the total weight of the composition, further, for example, ranging from 5% to 60% by weight, relative to the total weight of the composition, even further, for example, from 5% to 30% by weight, relative to the total weight of the composition, and further, for example, from 5% to 20% by weight, relative to the total weight of the composition.

The weight ratio of the at least one anionic surfactant to the at least one other surfactant may range, for example, from 1:1 to 30:1, further, for example, from 2:1 to 20:1 and even further, for example, from 3:1 to 10:1.

In one embodiment, the starch hydrolyzate has a DE ranging, for example, from 1 to 18 and further, for example, ranging from 1 to 16, and even further, for example, from 2 to 16.

The maltodextrins used in the compositions disclosed herein may be obtained by partial acid and/or enzymatic hydrolysis of the starch. Various hydrolysis processes are known and have been described in general on pages 511 and 512 of the book Encyclopedia of Chemical Technology by Kirk-Othmer, 3rd Ed., Vol. 22, 1978.

The starch undergoing this hydrolysis may originate from a varied source, for example, from maize, potato flour, tapioca, rice or cassaya. The hydrolyzates may undergo chemical changes such as, for example, an acetylation.

The maltodextrins that may used in the compositions disclosed herein may, for example, be in the form of a white powder or a concentrated solution.

The maltodextrins may, for example, be chosen from products sold by the company Roquette under the names GLUCIDEX/1W (DE<3), 2 (DE<3), 6 (DE 5-8), 6B (DE 4-8), 9 (DE 8-10), 12 (DE 11-14), 17 (DE 15-18), and under the names GLUCIDEX/IT6 (DE 5-8) and IT12 (DE 11-14), the origin of these maltodextrins being maize starch.

Further, the maltodextrins may, for examples be chosen from products sold by the company National Starch under the names N-ZORBIT/(DE<5) and CRYSTAL GUM S/(DE<5), the origin of these maltodextrins being cassaya starch.

For example, the maltodextrins may, for example, be chosen from products sold by the company Avebe under the names AVEBE MD 14, which originate from potato flour.

The fructans and fructosans may, for example, be chosen from oligosaccharides and polysaccharides comprising a sequence of anhydrofructose units optionally comprising at least one saccharide residue other than fructose. Fructans may, for-example, be linear or branched. Fructans may be products obtained directly from a plant or microbial source, or alternatively products whose chain length has been modified (lengthened or shortened) by fractionation, synthesis or hydrolysis, for example, enzymatic hydrolysis. Fructans may, for example, have a degree of polymerization ranging from 2 to 1000, for example, from 3 to 60.

Three groups of fructans may be distinguished. The first group comprises products whose fructose units are mostly linked via $\beta$-2-1 bonds. These are essentially linear fructans such as inulins.

The second group also comprises fructans, but the fructose units are essentially linked via $\beta$-2-6 bonds. These products are levans.

The third group comprises mixed fructans, for example, fructans comprising $\beta$-2-6 and $\beta$-2-1 sequences. These are essentially branched fructans such as graminans.

For example, the fructans may be chosen from inulins, for example, nonionic inulins. The inulins may be obtained, for example, from chicory, from dahlia or from Jerusalem artichoke.

The at least one polysaccharide may be present in the compositions disclosed herein in an amount ranging from 0.01% to 5% by weight, relative to the total weight of the composition, for example, ranging from 0.1% to 5% by weight, relative to the total weight of the composition, and further, for example, ranging from 0.2% to 3% by weight, relative to the total weight of the composition.

The cosmetic compositions disclosed herein may further comprise at least one agent for conditioning keratin materials.

Thus further disclosed herein are cosmetic compositions also comprising at least one conditioner.

When these compositions are applied to the hair, they may have at least one of the following good hair conditioning properties: treated hair is smooth, disentangles easily, and feels soft; hair has a natural, unladen appearance; and the hair has more volume and is easy to shape.

The compositions disclosed herein comprising at least one conditioner can be stable: for example, no uncontrolled release of the at least one conditioner or thickener from the composition takes place over time. Finally, the composition scan have a fondant, non-runny texture. The foam can easily be rinsed out.

When the composition comprises at least one conditioner, the at least one conditioner may, for example, be chosen from synthetic oils such as polyolefins, fluoro oils, fluoro waxes, fluoro gums, carboxylic acid esters, cationic polymers, silicones, mineral, plant oils, animal oils, plant waxes, ceramides and pseudoceramides.

The polyolefins may, for example, be poly-$\alpha$-olefins such as poly-$\alpha$-olefins chosen from:

hydrogenated and nonhydrogenated polybutene type poly-$\alpha$-olefins, for example, hydrogenated and nonhydrogenated polyisobutenes. Isobutylene oligomers with a molecular weight of less than 1000 and mixtures thereof with polyisobutylenes with a molecular weight of greater than 1000, for example, ranging from 1000 to 15000, may be used. The poly-$\alpha$-olefins that may be used in the compositions disclosed herein may, for example, be chosen from polyisobutenes sold under the name PERMETHYL 99 A, 101 A, 102 A, 104 A (n=16) and 106 A (n=38) by the company Presperse Inc., and the products sold under the name ARLAMOL HD (n=3) by the company ICI (wherein n is the degree of polymerization), and hydrogenated and nonhydrogenated polydecene type poly-$\alpha$-olefins. Such products are sold, for example, under the names ETHYLFLO by the company Ethyl Corp. and ARLAMOL PAO by the company ICI.

The mineral oils that may be used in the compositions disclosed herein may, for example, be chosen from hydrocarbons, such as hexadecane, and liquid paraffin.

The animal and plant oils that may be used may be chosen, for example, from sunflower oil, maize oil, soybean oil, avocado oil, jojoba oil, marrow oil, grapeseed oil, sesame oil, hazelnut oil, fish oils, glyceryl tricaprocaprylate, plant and animal oils of formula $R_9COOR_{10}$ wherein $R_9$ is chosen from higher fatty acid residues comprising from 7 to 29 carbon atoms and $R_{10}$ is chosen from linear and branched hydrocarbon-based chains comprising from 3 to 30 carbon atoms. In one embodiment, the plant and animal oils of formula $R_9COOR_{10}$ may be chosen from alkyl and alkenyl, natural and synthetic essential oils, for example, from eucalyptus oil, lavandin oil, lavender oil, vetiver oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil.

The plant waxes useful herein may be chosen, for instance, from carnauba wax, candelilla wax, ozokerite, olive wax, rice wax, hydrogenated jojoba wax, the absolute waxes of flowers, and marine waxes. One example of an absolute wax of a flower is the essential wax of blackcurrant flower.

The ceramides and pseudo ceramides useful herein as conditioners may be chosen, for example, from ceramides and pseudoceramides corresponding to formula (VIII):

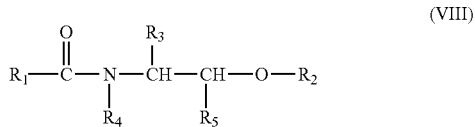

(VIII)

wherein:
  $R_1$ is chosen from:
    either saturated and unsaturated, linear and branched $C_1$–$C_{50}$ hydrocarbon-based radicals; such as $C_5$–$C_{50}$ hydrocarbon-based radicals, it being possible for the $C_1$–$C_{50}$ hydrocarbon-based radicals to be substituted with at least one hydroxyl group which can be esterified with an acid $R_7COOH$, wherein $R_7$ is chosen from saturated and unsaturated, linear and branched, $C_1$–$C_{35}$ hydrocarbon-based radicals optionally hydroxylated with at least one hydroxyl group, wherein the at least one hydroxyl group of the radical $R_7$ may be esterified with saturated and unsaturated, linear and branched, optionally mono- and polyhydroxylated $C_1$–$C_{35}$ fatty acids;
    or a radical R"—(NR—CO)—R', wherein R is chosen from a hydrogen atom and mono-and polyhydroxylated $C_1$–$C_{20}$ hydrocarbon-based radicals, such as monohydroxylated $C_1$–$C_{20}$ hydrocarbon-based radicals, R' and R", which may be identical or different, are each chosen from hydrocarbon-based radicals, the sum of the carbon atoms ranging from 9 to 30, and R' is a divalent radical;
    or a radical $R_8$—O—CO—$(CH_2)_p$, wherein $R_8$ is chosen from $C_1$–$C_{20}$ hydrocarbon-based radicals, and p is an integer ranging from 1 to 12;
  $R_2$ is chosen from a hydrogen atom; a saccharide type radical, chosen, for example, from $(glycosyl)_n$, $(galactosyl)_m$ and sulfogalactosyl radicals, wherein n is an integer ranging from 1 to 4 and m is an integer ranging from 1 to 8; sulfate and phosphate residues; a phosphorylethylamine radical; and a phosphorylethylammonium radical;
  $R_3$ is chosen from a hydrogen atom and saturated and unsaturated $C_1$–$C_{33}$ hydrocarbon-based radicals optionally hydroxylated with at least one hydroxyl group, it being possible for the at least one hydroxyl group to be esterified with an inorganic acid or an acid $R_7COOH$, wherein $R_7$ has the same meanings as above, it being possible for the at least one hydroxyl to be etherified with at least one radical chosen from $(glycosyl)_n$, $(galactosyl)_m$, sulfogalactosyl, phosphorylethylamine and phosphorylethylammonium radicals, it being also possible for $R_3$ to be substituted with at least one radical chosen from $C_1$–$C_{14}$ alkyl radicals;
  $R_4$ is chosen from a hydrogen atom, methyl and ethyl radicals, saturated and unsaturated, linear and branched, optionally hydroxylated $C_3$–$C_{50}$ hydrocarbon-based radicals and a radical —$CH_2$—CHOH—$CH_2$—O—$R_6$ wherein $R_6$ is chosen from $C_{10}$–$C_{26}$ hydrocarbon-based radicals and radical $R_8$—O—CO—$(CH_2)_p$, wherein $R_8$ is chosen from $C_1$–$C_{20}$ hydrocarbon-based radicals, and p is an integer ranging from 1 to 12;
  $R_5$ is chosen from a hydrogen atom and saturated and unsaturated, linear and branched, $C_1$–$C_{30}$ hydrocarbon-based radicals optionally hydroxylated with at least one hydroxyl group, it being possible for the at least one hydroxyl to be etherified with at least one radical chosen from $(glycosyl)_n$, $(galactosyl)_m$, sulfogalactosyl, phosphorylethylamine and phosphorylethylammonium radicals, with the proviso that when $R_3$ and $R_5$ are both a hydrogen atom or when $R_3$ is a hydrogen atom and $R_5$ is a methyl radical, then $R_4$ is not a hydrogen atom, a methyl radical, or an ethyl radical.

In one embodiment, $R_3$ is chosen from $C_{15}$–$C_{26}$ α-hydroxyalkyl radicals, wherein the hydroxyl group is optionally esterified with at least one acid chosen from $C_{16}$–$C_{30}$ α-hydroxy acids.

For example, the ceramides useful herein may be chosen from at least one of:
  2-N-linoleoylaminooctadecane-1,3-diol,
  2-N-oleoylaminooctadecane-1,3-diol,
  2-N-palmitoylaminooctadecane-1,3-diol,
  2-N-stearoylaminooctadecane-1,3-diol,
  2-N-behenoylaminooctadecane-1,3-diol,
  2-N-[2-hydroxypalmitoyl]aminooctadecane-1,3-diol,
  2-N-stearoylamindoctadecane-1,3,4-triol,
  2-N-palmitoylaminohexadecane-1,3-diol,
  bis(N-hydroxetyl-N-cetyl)malonamide
  N-(2 hydroxyethyl)-N-(3-cetyloxy-2-hydroxypropyl) cetylamide, and
  N-docosanoyl-N-methyl-D-glucamine.

In one embodiment, the compositions disclosed herein may further comprise at least one cationic polymer.

As used herein, the term "cationic polymer" means any polymer comprising at least one group chosen from cationic groups and groups that may be ionized into cationic groups.

The cationic polymers that may be used in the compositions disclosed herein may, for example, be chosen from at least one cationic polymer already known per se as improving the cosmetic properties of hair treated with detergent compositions, for example, those described in Patent Application No. EP-A-337 354 and in French Patent Application Nos. FR-A-2 270 846, 2 383 660, 2 598 611, 2 470 596 and 2 519 863.

The at least one cationic polymer may, for example, be chosen from polymers comprising units comprising at least one group chosen from primary, secondary, tertiary and quaternary amine groups, that may form part of the main polymer chain and/or be borne by at least one side substituent directly attached to the main polymer chain.

The at least one cationic polymer used in the compositions disclosed herein may have a number-average molecular mass ranging from 500 to $5\times10^6$ and, for example, ranging from $10^3$ to $3\times10^6$.

In one embodiment, the at least one cationic polymer may, for example, be chosen from polyamine, polyamino amide and polyquaternary ammonium type polymers. These polymers are known products. For example, the polyamine, polyamino amide and polyquaternary ammonium type polymers that may be used in the compositions disclosed herein may, for example, be chosen from those polymers described in French Patent Nos. 2 505 348 and 2 542 997.

For example, the at least one cationic polymer may be chosen from the following families:

(1) Homopolymers and copolymers derived from acrylic, methacrylic esters and amides and comprising at least one unit of the following formulae:

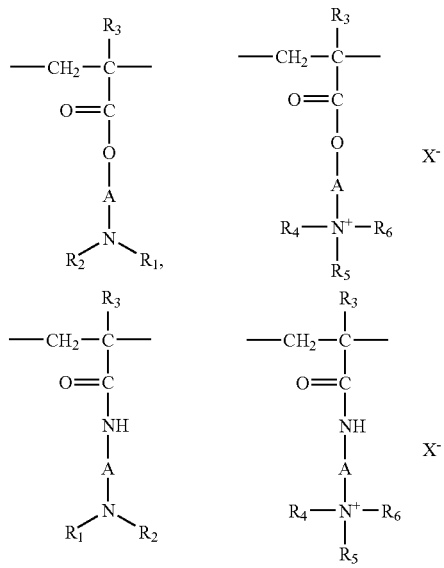

wherein:
  $R_3$, which may be identical or different, is chosen from a hydrogen atom and a $CH_3$ radical;
  A, which may be identical or different, is chosen from linear and branched alkyl groups comprising from 1 to 6 carbon atoms, for example, 2 or 3 carbon atoms, and hydroxyalkyl groups comprising from 1 to 4 carbon atoms;
  $R_4$, $R_5$, $R_6$, which may be identical or different, are each chosen from alkyl groups comprising from 1 to 18 carbon atoms, a benzyl group and, for example, alkyl groups comprising from 1 to 6 carbon atoms;
  $R_1$ and $R_2$, which may be identical or different, are each chosen from a hydrogen atom and alkyl groups comprising from 1 to 6 carbon atoms, for example, methyl groups and ethyl groups;
  $X^-$ is an anion chosen from anions derived from a mineral and organic acids, such as a methylsulfate anion and halides such as chloride and bromide.

The copolymers of family (1) can further comprise at least one unit derived from comonomers which may be chosen from acrylamides, methacrylamides, diacetone acrylamides, acrylamides and methacrylamides substituted on the nitrogen atom by at least one group chosen from lower,($C_1$–$C_4$) alkyls, acrylic and methacrylic acids and esters, thereof, vinyllactams such as vinylpyrrolidone and vinylcaprolactam, and vinyl esters.

For example, the copolymers of family (1) may be chosen from:
  copolymers of acrylamide and of dimethylaminoethyl methacrylate quaternized with dimethyl sulfate or with a dimethyl halide, such as the product sold under the name Hercofloc® by the company Hercules,
  copolymers of acrylamide and of methacryloyloxyethyltrimethylammonium chloride described, for example, in Patent Application No. EP-A-080 976 and sold under the name Bina Quat® P 100 by the company Ciba Geigy,
  copolymers of acrylamide and of methacryloyloxyethyltrimethylammonium methosulfate sold under the name Reten® by the company Hercules,
  quaternized and nonquaternized vinylpyrrolidone/dialkylaminoalkyl acrylate and methacrylate copolymers, such as the products sold under the name "Gafquat®" by the company ISP, such as, for example, "Gafquat® 734" and "Gafquat®755", or alternatively the products known as "Copolymer 845, 958 and 937". These polymers are described in detail in French Patent Nos. 2 077 143 and 2 393 573,
  dimethylaminoethyl methacrylate/vinylcaprolactam/vinylpyrrolidone terpolymers, such as the product sold under the name Gaffix® VC 713 by the company ISP,
  vinylpyrrolidone/methacrylamidopropyldimethylamine copolymers sold, for example, under the name Styleze® CC 10 by ISP, and
  quaternized vinylpyrrolidone/dimethylaminopropylmethacrylamide copolymers, such as the product sold under the name "Gafquat® HS 100" by the company ISP.

(2) The cellulose ether derivatives comprising at least one quaternary ammonium group, described in French Patent No. 1 492 597, for example, the polymers sold under the names "JR" (JR 400, JR 125 and JR 30M) and "LR",(LR 400 or LR 30M) by the company Union Carbide Corporation. These polymers are also defined in the CTFA dictionary as quaternary ammoniums of hydroxyethylcellulose that have reacted with an epoxide substituted with at least one trimethylammonium group.

(3) Cationic cellulose derivatives such as cellulose copolymers and cellulose derivatives grafted with at least one water-soluble quaternary ammonium monomer, and described, for example, in U.S. Pat. No. 131,576, such as hydroxyalkylcelluloses, for example, hydroxymethyl-, hydroxyethyl- and hydroxypropylcelluloses grafted, for example, with at least one salt chosen from methacryloylethyltrimethylammonium, methacrylamidopropyltrimethylammonium and dimethyldiallylammonium salts.

The commercial products corresponding to this definition are, for example, the products sold under the names "Celquate L 200" and "Celquat® H $100_5$" by the company National Starch.

(4) The cationic polysaccharides described, for example, in U.S. Pat. Nos. 3,589,578 and 4,031,307, such as guar gums comprising at least one cationic trialkylammonium group. The cationic polysaccharides may, for example, be chosen from guar gums modified with a salt, for example, the chloride of 2,3-epoxypropyltrimethylammonium.

Such products are sold, for example, under the trade names Jaguar® C13 S, Jaguar® C 15, Jaguar® C 17 and Jaguar® C162 by the company Rhodia Chimie.

(5) Polymers comprising at least one piperazinyl unit and at least one radical chosen from divalent alkylene and hydroxyalkylene radicals, wherein the divalent alkylene and hydroxyalkylene radicals comprise at least one group chosen from straight and branched chains, optionally interrupted by at least one entity chosen from oxygen, sulfur and nitrogen atoms, aromatic rings and heterocyclic rings; and the oxidation and/or quaternization products of these polymers. Such polymers are described, for example, in French Patent Nos. 2 162 025 and 2 280 361;

(6) Water-soluble polyamino amides prepared, for example, by polycondensation of an acidic compound with a polyamine; these polyamino amides can be crosslinked by at least one crosslinking agent chosen from epihalohydrins, diepoxides, dianhydrides, unsaturated dianhydrides, bis-unsaturated derivatives, bis-halohydrins, bis-azetidiniums, bis-haloacyidiamines, bis-alkyl halides and from oligomers resulting from the reaction of a difunctional compound which is reactive with bis-halohydrin, bis-azetidinium, bis-haloacyldiamine, bis-alkyl halide, epihalohydrin, diepoxide and bis-unsaturated derivative; wherein the at least one crosslinking agent is used in an amount ranging from 0.025 to 0.35 mol per amine group of the polyamino amides. These polyamino amides can be alkylated or, if they comprise at least one tertiary amine functional group, they can be quaternized. Such polymers are described, for example, in French Patent Nos. 2 252 840 and 2 368 508;

(7) Polyamino amide derivatives resulting from the condensation of polyalkylene polyamines with polycarboxylic acids followed by alkylation with difunctional agents. The polyaminoamido derivatives may, for example, be chosen from adipic acid/dialkylaminohydroxyalkyl-dialkylenetriamine polymers wherein the alkyl radical comprises from 1 to 4 carbon atoms and, for example, is chosen from methyl, ethyl and propyl groups. Such polymers are described, for example, in French Patent No. 1 583 363.

For example, the polyamidoamino derivatives may be chosen from adipic acid/dimethylaminohydroxypropyl/diethylenetriamine polymers sold under the name "CARTARETINE F. F4 or F8" by the company Sandoz.

(8) Polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio of the polyalkylene polyamine to the dicarboxylic acid ranges from 0.8:1 to 1.4:1. The polyamino amide resulting therefrom is reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

For example, polymers of this type are sold under the name "Hercosett® 57" by the company Hercules Inc. and under the name "PD 170" or "Delsette® 101" by the company Hercules in the case of the adipic acid/epoxypropyl/diethylenetriamine copolymer.

(9) Cyclopolymers of alkyldiallylamine and of dialkyldiallylammonium, such as the homopolymers and copolymers comprising, as a main constituent of the chain, at least, one unit chosen from units corresponding to formulas (IX(a)) and (IX(b)):

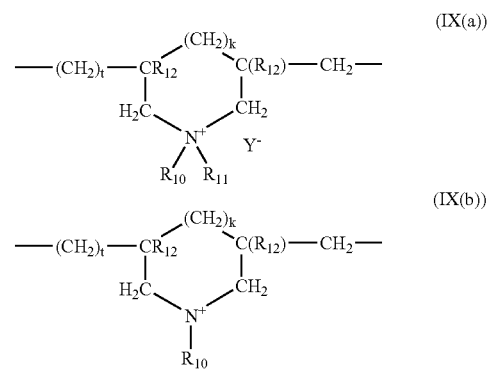

wherein:
k and t are each equal to 0 or 1, the sum k+t being equal to 1;
$R_{12}$, which may be identical or different, is chosen from a hydrogen atom and a methyl radical;
$R_{10}$ and $R_{11}$, which may be identical or different, are each chosen from alkyl, groups comprising from 1 to 22 carbon atoms, hydroxyalkyl groups wherein the alkyl group may, for example, be chosen from alkyl groups comprising from 1 to 5 carbon atoms, lower ($C_1$–$C_4$) amidoalkyl groups, or $R_{10}$ and, $R_{11}$ can form, together with the nitrogen atom to which they are attached, a heterocyclic group such as a piperidyl group and a morpholinyl group; and
$Y^-$ is an anion chosen from bromide, chloride, acetate, borate, citrate, tartrate, bisulfate, bisulfite, sulfate and phosphate anions.

These polymers are described, for example, in French Patent No. 2 080 759 and in its Certificate of Addition 2 190 406.

In one embodiment, $R_{10}$ and $R_{11}$, which may be identical or different, can each be chosen from alkyl groups comprising from 1 to 4 carbon atoms.

For example, the cyclopolymers of alkyldiallylamine and of dialkyldiallylammonium may be chosen from the homopolymers of dimethyldiallylammonium chloride sold under the name "Merquat® 100" by the company Nalco (and its homologs of low weight-average molecular mass) and the copolymers of diallyidimethylammonium chloride and of acrylamide, sold under the name "MERQUAT 550".

(10) The quaternary diammonium polymer comprising repeating units corresponding to formula (X):

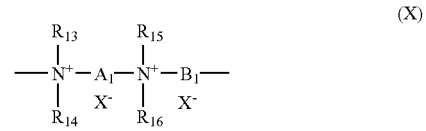

wherein:
$R_{13}$, $R_{14}$, $R_{15}$ and $R_{16}$, which may be identical or different, are each chosen from aliphatic, alicyclic, and arylaliphatic radicals comprising from 1 to 20 carbon atoms and from lower hydroxyalkylaliphatic radicals, or $R_{13}$, $R_{14}$, $R_{15}$ and $R_{16}$, together or separately, form, with the nitrogen atom to which they are attached, at least one heterocycle optionally comprising a second hetero atom other than nitrogen, or alternatively $R_{13}$, $R_{14}$, $R_{15}$ and $R_{16}$, which may be identical or different, are each chosen from linear and branched $C_1$–$C_6$ alkyl radicals substituted by at least one group chosen from nitrile, ester, acyl, amide, —CO—O—$R_{17}$—D, and —CO—NH—$R_{17}$—D groups, wherein $R_{17}$, Which may be identical or different, is chosen from alkylene groups and D, which may be identical or different, is chosen from quaternary ammonium groups;

$A_1$ and $B_1$, which may be identical or different, are each chosen from linear and branched, saturated and unsaturated, polymethylene groups comprising from 2 to 20 carbon atoms and which may comprise, linked to or intercalated in the main chain, at least entity chosen from aromatic rings, oxygen and sulfur atoms and sulfoxide, sulfone, disulfide, amino, alkylamino, hydroxyl, quaternary ammonium, ureido, amide and ester groups, and $X^-$ is an anion chosen from anions derived from mineral and organic acids;

$A_1$, $R_{13}$ and $R_{15}$ can form, with the two nitrogen atoms to which they are attached, a piperazine ring; in addition, if $A_1$ is chosen from linear and branched, saturated and unsaturated alkylene and hydroxyalkylene radicals, $B_1$ can also be chosen from groups of the following formula:

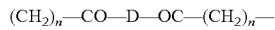

wherein D is chosen from:

a) glycol residues of formula: —O—Z—O—, wherein Z is chosen from linear and branched hydrocarbon-based radicals and groups corresponding to the following formulae:

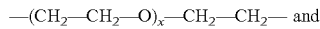

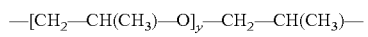

wherein x and y, which may be identical or different, are each an integer ranging from 1 to 4, representing a defined and unique degree of polymerization or any number ranging from 1 to 4 representing an average degree of polymerization;

b) bis-secondary diamine residues such as piperazine derivatives;

c) bis-primary diamine residues of formula: —NH—Y—NH—, wherein Y is chosen from linear and branched hydrocarbon-based radicals and the divalent radical

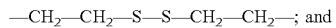

d) a ureylene group of formula: —NH—CO—NH—; and n ranges from 1 to 6.

For example, $X^-$ can be an anion such as chloride or bromide.

These polymers have a number-average molecular mass which may range, for example, from 1000 to 100 000.

These polymers are described, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, polymers that comprise repeating units corresponding to the formula (XI) below can be used:

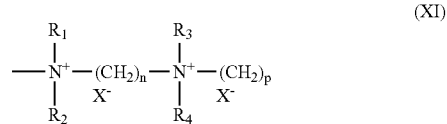

wherein: $R_1$, $R_2$, $R_3$ and $R_4$, which may be identical or different, are each chosen from alkyl and hydroxyalkyl radicals comprising from 1 to 4 carbon atoms, n and p, which may be identical or different, are each integers ranging from 2 to 20, and $X^-$ is an anion chosen from anions derived from mineral and organic acids.

For example, a polymer comprising repeating units of formula (XI) can be used in the compositions disclosed herein, wherein $R_1$, $R_2$, $R_3$ and $R_4$ are each a methyl radical, n=3, p=6 and X=Cl, referred to as hexadimethrine chloride according to the INCl nomenclature (CTFA).

(11) Polyquaternary Ammonium Polymers Comprising Units of Formula (XII):

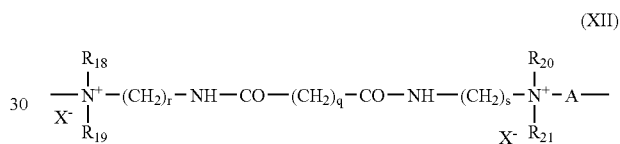

wherein:
$R_{18}$, $R_{19}$, $R_{20}$ and $R_{21}$, which may be identical or different, are each chosen from a hydrogen atom and methyl, ethyl, propyl, β-hydroxyethyl, β-hydroxypropyl and $CH_2CH_2(OCH_2CH_2)_pOH$ radicals, wherein p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are each integers ranging from 1 to 6, q is equal to 0 or to an integer ranging from 1 to 34, $X^-$ is chosen from anions, such as halides, A is chosen from dihalide radicals and, for example, a a —$CH_2$—$CH_2$—O—$CH_2$—$CH_2$— group.

Such polymers are described, for example, in Patent Application No. EP-A-122 324.

The polyquaternary ammonium polymers comprising units of formula (XII) may, for example, be chosen from the products "Mirapol® A 15", "Mirapol® AD1", "Mirapol® AZ1" and "Mirapol® 175" sold by the company Miranol.

(12) Quaternary polymers of vinylpyrrolidone and of vinylimidazole, for example, the products sold under the names Luviquat® FC 905, FC 550 and FC 370 by the company BASF.

(13) Polyamines such as Polyquart® H sold by Cognis, which is given under the: reference name "Polyethylene glycol (15) tallow polyamine" in the CTFA dictionary.

(14) Crosslinked methacryloyloxy($C_1$–$C_4$)alkyltri($C_1$–$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. It is also possible to use a crosslinked acrylamide/methacryloyloxyethyltrimethylammonium chloride copolymer (20/80 by weight) in the form of a dispersion comprising 50% by weight of said copolymer in mineral oil, for example. This dispersion is sold under the name "Salcare® SC 92" by the company Ciba. It is also possible to use a crosslinked methacryloyloxyethyltrimethylammonium chloride homopolymer comprising about 50% by weight of the homopolymer in mineral oil or in a liquid ester, for example. These dispersions are sold under the names "Salcare® SC 95" and "Salcare® SC 96" by the company Ciba.

The cationic polymers that can be used in the compositions disclosed herein may also, for example, be chosen from cationic proteins, cationic protein hydrolyzates, polyalkyleneimines, for example, polyethyleneimines, polymers comprising at least one unit chosen from vinylpyridine and vinylpyridinium units, condensates of polyamines and of epichlorohydrin, quaternary polyureylenes and chitin derivatives.

The cationic polymers that may be used in the compositions disclosed herein may, for example, be chosen from quaternary cellulose ether derivatives such as the products sold under the name "JR 400" by the company Amerchol, cationic cyclopolymers, for example, the dimethyldiallylammonium chloride homopolymers and copolymers sold under the names "Merquat® 100", "Merquat® 550" and "Merquat® S" by the company Nalco, cationic polysaccharides such as guar gums modified with a 2,3-epoxypropyltrimethylammonium salt, and quaternary polymers of vinylpyrrolidone and of vinylimadazole.

The cationic polymers may, for example, be present in an amount ranging from 0.001% to 10% by weight, relative to the total weight of the composition, for example, from 0.005% to 5% by weight, relative to the total weight of the composition, and further, for example, from 0.01% to 3% by weight, relative to the total weight of the composition.

The silicone's that may be used in the compositions disclosed herein may, for example, be chosen, from polyorganosiloxanes that are insoluble in the composition and that may be in the form of oils, waxes, resins and gums.

The viscosity of the silicones is measured, for example, at 25° C. according to ASTM standard 445 Appendix C.

The organopolysiloxanes are defined, for example, in greater detail in Walter Noll's "Chemistry and Technology of Silicones" (1968) Academic Press. The organopolysiloxanes can be chosen from volatile and nonvolatile organopolysiloxanes.

When they are chosen from volatile organopolysiloxanes, the silicones may, for example, be chosen from volatile organopolysiloxanes having a boiling point ranging from 60° C. to 260° C., and further, for example, may be chosen from:
(i) cyclic silicones comprising from 3 to 7, for example, from 4 to 5 silicon atoms. These cyclic silicones may, for example, be chosen from at least one of octamethylcyclotetrasiloxane sold, for example, under the name "VOLATILE SILICONE 7207" by Union Carbide and "SILBIONE 70045 V 2" by Rhodia Chimie, decamethylcyclopentasiloxane sold under the name "VOLATILE SILICONE 7158" by Union Carbide, and "SILBIONE 70045 V 5" by Rhodia Chimie. The cyclic silicones may also, for example, be chosen from dimethylsiloxane/methylalkylsiloxane type cyclocopolymers for use in the compositions disclosed herein, such as "SILICONE VOLATILE FZ 3109" sold by the company Union Car-bide, having the following formula:

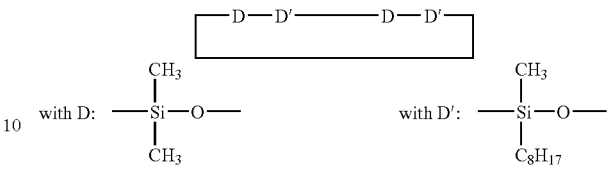

The cyclic silicones may also, for example, be chosen from mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy) neopentane;

(ii) linear volatile silicones comprising from 2 to 9 silicon atoms and having a viscosity of less than or equal to $5 \times 10^{-6}$ m$^2$/s at 25° C. For example, decamethyltetrasiloxane sold under the name "SH 200" by the company Toray Silicone. Silicones belonging to this category are also described in the article published in Cosmetics and Toiletries, Vol. 91, Jan. 76, pp. 27–32, Todd & Byers "Volatile Silicone Fluids for Cosmetics".

Nonvolatile silicones, for example, non-volatile silicones chosen from at least one of polyalkylsiloxanes, polyarylsiloxanes, polyalkylarylsiloxanes, silicone gums and resins, and polyorganosiloxanes modified with at least one organo-functional group may be used.

These non-volatile silicones may, for example, be chosen from polyalkylsiloxanes, for example, polyalkylsiloxanes chosen from polydimethylsiloxanes comprising trimethylsilyl end groups having a viscosity ranging from $5 \times 10^{-6}$ to $-2.5$ m$^2$ in at 25° C., for example, ranging from $1 \times 10^{-5}$ to 1 m$^2$/s.

The polyalkylsiloxanes may, for example, be chosen from the following commercial products:
the oils of the Mirasil series sold by the company Rhodia Chimie, such as, the oil MIRASIL DM 500 000;
the oils of the 200 series from the company Dow Corning, such as, DC200 with a viscosity of 60 000 cSt;
the Viscasil oils from General Electric and certain oils of the SF series (SF 96, SF 18) from General Electric.

The polyalkylsiloxanes may also, for example, be chosen from polydimethylsiloxanes comprising dimethylsilanol end groups (Dimethiconol according to the CTFA name) such as the oils of the 48 series from the company Rhodia Chimie.

In this category of polyalkylsiloxanes, the polyalkylsiloxanes may further be chosen from the products sold under the names "ABIL WAX 9800 and 9801" by the company Goldschmidt, which are poly($C_1$–$C_{20}$)alkylsiloxanes.

The polyalkylarylsiloxanes may, for example, be chosen from linear and branched polydimethylmethylphenylsiloxanes and polydimethyldiphenylsiloxanes, with a viscosity ranging from $1 \times 10^{-5}$ to $5 \times 10^{-2}$ m$^2$/s at 25° C.

These polyalkylarylsiloxanes may further be chosen, for example, from the products sold under the following names:
MIRASIL DPDM oils from Rhodia Chimie;
oils of the RHODORSIL 70 633 and 763 series from Rhodia Chimie;
Dow Corning 556 Cosmetic Grade Fluid oil from Dow Corning;

silicones of the PK series from Bayer, such as the product PK20;

silicones of the PN and PH series from Bayer, such as the products PN1000 and PH1000;

certain oils of the SF series from General Electric, such as SF 1023, SF1154, SF 1250, and SF1265.

The silicone gums that can be used in the compositions disclosed herein may, for example, be chosen from polydiorganosiloxanes having high number-average molecular masses ranging from 200 000 to 1 000 000, used alone or as a mixture in a solvent. This solvent can be chosen, for example, from at least one of volatile silicones, polydimethylsiloxane (PDMS) oils, polyphenylmethylsiloxane (PPMS) oils, isoparaffins, polyisobutylenes, methylene chloride, pentane, dodecane and tridecane.

The silicone gums may, for example, be chosen from:
polydimethylsiloxane,
polydimethylsiloxane/methylvinylsiloxangums,
polydimethylsiloxane/diphenylsiloxane,
polydimethylsilixane/phenylmethylsiloxane, and
polydimethylsiloxane/diphenylsiloxane/methylvinylsiloxane.

The silicone gums may further, for example; be chosen from the following mixtures:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the, CTFA dictionary), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500 000', dissolved in the oil SF 1202 SILICONE FLUID corresponding to decamethylcyclopentasiloxane; and, mixtures of two PDMSs of different viscosities, and for example, of a PDMS gum and a PDMS oil, such as the product SF 1236 from the company General Electric. The product SF 1236 is a mixture of an SE 30 gum defined above, having a viscosity of 20 m$^2$/s and an SF 96 oil, with a viscosity of 5×10$^{-6}$ m$^2$/s. This product, for example, comprises 15% SE 30 gum and 85% SF 96 oil.

The organopolysiloxane resins that can be used in the compositions disclosed herein may, for example, be chosen from crosslinked siloxane, systems comprising the following units: $R_2SiO_{2/2}$, $R_3SiO_{1/2}$, $RSiO_{3/2}$ and $SiO_{4/2}$ wherein R is chosen from hydrocarbon-based groups comprising 1 to 16 carbon atoms and a phenyl group. For example, the organopolysiloxane resins may be chosen from those resins wherein R is chosen from $C_1$–$C_4$ lower alkyl radicals, such as a methyl radical and from a phenyl radical.

For example, these resins may be chosen from the product sold under the name "Dow Corning 593" and those sold under the names "SILICONE FLUID SS 4230 and SS 4267" by the company General Electric, which are silicones having the dimethyl/trimethyl siloxane structure.

Further, for example, these resins may be chosen from the trimethyl siloxysilicate type resins sold, for example, under the names X22-4914, X21-5034 and X21-5037 by the company Shin-Etsu.

The organomodified silicones which can be used in the compositions disclosed herein may, for example, be chosen from silicones as defined above and comprising in its structure at least one organofunctional group attached via a hydrocarbon-based radical.

For example, the organomodified silicones may be chosen from the polyorganosiloxanes comprising at least one organofunctional group chosen from:

polyethyleneoxy and polypropyleneoxy groups optionally comprising at least one $C_6$–$C_{24}$ alkyl group, such as the products known as dimethicone copolyol sold, by the company Dow Corning under the name DC 1248 and the oils SILWET L 722, L 7500, L 77 and L 711 by the company Union Carbide, and the ($C_{12}$)alkylmethicone copolyol sold by the company Dow Corning under the name Q2 5200;

substituted and unsubstituted amine groups, such as the products sold under the name GP 4 SILICONE FLUID and GP 7100 by the company Genesee, and the products sold under the names Q2 8220 and Dow Corning 929 or 939 by the company Dow Corning. The substituted amine groups may, for example, be chosen from $C_1$–$C_4$ aminoalkyl groups;

thiol groups such as the products sold under the names "GP 72 A" and "GP 71" from Genesee;

alkoxylated groups such as the product sold under the name "SILICONE COPOLYMER F-755" by SWS Silicones and ABIL WAX 2428, 2434 and 2440 by the company Goldschmidt;

hydroxylated groups such as the polyorganosiloxanes comprising at least one hydroxyalkyl functional group, described in French Patent Application No. FR-A85/16334;

acyloxyalkyl groups such as the-polyorganosiloxanes described in U.S. Pat. No. 4,957,732;

anionic groups of carboxylic type, such as the products described in Patent. No. EP 186 507 from the company Chisso Corporation, and anionic groups of the alkylcarboxylic type, such as those present in the product X-22-3701E from the company Shin-Etsu; 2-hydroxyalkyl sulfonate; and 2-hydroxyalkyl thiosulfate such as the products sold by the company Goldschmidt under the names "ABIL S201" and "ABIL S255";

hydroxyacylamino groups, such as the polyorganosiloxanes described in Patent Application No. EP 342 834, for example, the product Q2-8413 from the company Dow Corning.

In one embodiment, it may also be possible to use silicones comprising a polysiloxane portion and a portion comprising a nonsilicone organic chain, wherein one of the two portions constitutes the main chain of the polymer and the other is grafted onto the main chain. These polymers are described, for example, in Patent Application Nos. EP-A-412 704, EP-A-412 707, EP-A-640 105, WO 95/00578, EP-A-582 152 and WO 93/23009 and U.S. Pat. Nos. 4,693, 935, 4,728,571 and 4,972,037. These polymers may, for example, be anionic or nonionic.

Such polymers may, for example, be the copolymers obtained by free-radical polymerization starting with a monomer mixture comprising:

a) 50 to 90% by weight of tert-butyl acrylate;

b) 0 to 40% by weight of acrylic acid; and c) 5 to 40% by weight of silicone macromer of formula:

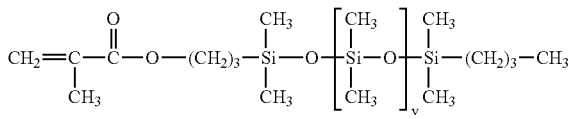

wherein v is a number ranging from 5 to 700; the weight percentages being calculated relative to the total weight of the monomers.

The grafted silicone polymers may, for example, be chosen from polydimethylsiloxanes (PDMS) onto which are grafted, via a thiopropylene type connecting chain unit, poly(meth)acrylic acid type and polyalkyl (meth)acrylate type mixed polymer units and polydimethylsiloxanes (PDMS) onto which are grafted, via a thiopropylene type connecting chain unit, polyisobutyl (meth)acrylate type polymer units.

As used herein, all of the silicones can also be in the form of emulsions.

For example, the polyorganosiloxanes used in the compositions disclosed herein may be chosen, for example, from:

nonvolatile silicones chosen from the family of polyalkylsiloxanes comprising trimethylsilyl end groups, such as oils having a viscosity ranging from 0.2 to 2.5 m$^2$/s at 25° C., such as the oils of the DC200 series from Dow Corning, for example, that with a viscosity of 60 000 cSt, of the MIRASIL DM series and further, for example, the oil Mirasil DM 500 000 sold by the company Rhodia Chimie and the silicone oil AK 300.000 from the company Wacker, the polyalkylsiloxanes comprising dimethylsilanol end groups such as dimethiconols and polyalkylarylsiloxanes, such as the oil MIRASIL DPDM sold by the company Rhodia Chimie;

polysiloxanes comprising at least one amine group, such as amodimethicones and trimethylsilylamodimethicones.

As disclosed herein, the ceramide type compounds useful as conditioners in the composition disclosed herein may be chosen, for example, from natural and synthetic ceramides, glycoceramides, pseudoceramides and neoceramides.

The ceramide type compounds, may be chosen, for example, from those described in Patent Application Nos. DE 4 424 530, DE 4 424 533, DE 4 402 929, DE 4 420 736, WO 95/23807, WO 94/07844, EP-A-0 646 572, WO 95/16665, FR-2 673 179, EP-A-0 227 994, WO 94/07844, WO 94/24097 and WO 94/10131, the teachings of which are included herein by way of reference.

The ceramide type compounds may, for example, be chosen from at least one of:
2-N-linoleoylaminooctadecane-1,3-diol,
2-N-oleoylaminooctadecane-1,3-diol,
2-N-palmitoylaminooctadecane-1,3-diol,
2-N-stearnoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol, for example, N-stearoylphytosphingosine,
2-N-palmitoylaminohexadecane-1,3-diol
bis(N-hydroxyethyl-N-cetyl)malonamide,
N-(2-hydroxyethyl)-N-(3-cetyloxy-2-hydroxypropyl) cetylamide; and
N-docosanoyl-N-methyl-D-glucamine.

The carboxylic acid esters that may be used as conditioners in the compositions disclosed herein may, for example, be chosen from saturated and unsaturated, linear and branched $C_{10}$–$C_{30}$ aliphatic monocarboxylic, dicarboxylic and tricarboxylic acid esters of saturated and unsaturated, linear and branched $C_1$–$C_8$ aliphatic alcohols and polyols, and saturated and unsaturated, linear and branched $C_2$–$C_8$ aliphatic monocarboxylic, dicarboxylic and tricarboxylic acid esters of saturated and unsaturated, linear and branched $C_{10}$–$C_{30}$ aliphatic alcohols and polyols.

For example, the carboxylic acid esters may be chosen from cetyl lactate; $C_{12}$–$C_{15}$ alkyl lactate, isostearyl lactate; lauryl lactate, linoleyl lactate; oleyl lactate; ethyl palmitate and isopropyl palmitate, $C_1$–$C_5$ alkyl myristates such as isopropyl myristate and butyl myristate, isobutyl stearate; dioctyl malate, hexyl laurate, and 2-hexyldecyl laurate.

In one embodiment, the at least one conditioner may be chosen from cationic polymers and silicones, and mixtures thereof.

The at least one conditioner may be dispersed in the compositions in the form of particles having a mean size, for example, by volume (measured by one of the techniques described in the article Particle Size Analysis, Anal. Chem. 1995, 67, 257–272) ranging, for example, from 2 nanometers to 100 microns, further, for example, from 10 nm to 50 microns.

As used herein, the at least one conditioner may be present in an amount ranging, for example, from 0.0001 to 20% by weight, relative to the total weight of the composition, for example, 0.001% to 10% by weight and further, for example, from 0.005% to 5% by weight, and even further, for example, from 0.005 to 3% by weight, and still further, for example, from 0.01% to 3% by weight, relative to the total weight of the composition.

The cosmetically acceptable medium may be chosen, for example, from water and mixtures of water and at least one solvent chosen from cosmetically and derma-tologically acceptable solvents such as monoalcohols, polyalcohols and glycol ethers. The water may, for example, be present in an amount ranging from 30% to 98% by weight, relative to the total weight of the composition, further, for example, from 50% to 98% by weight, relative to the total weight of the composition.

For example, the at least one solvent may be chosen from monoalcohols such as ethanol and isopropanol, polyalcohols such as diethylene glycol and glycerol, glycol ethers, and alkyl ethers of glycol and of diethylene glycol.

The compositions disclosed herein may have, for example, a final pH, for example, ranging from 3 to 10. This pH may range further, for example, from 4 to 8. The pH may be adjusted to the desired value in a conventional manner by adding at least one base chosen from organic and mineral bases to the composition, for example, at least one base chosen from aqueous ammonia and primary, secondary and tertiary (poly)amines, such as monoethanolamine, diethanolamine, triethanolamine, isopropanolamine and 1,3-propanediamine, or alternatively by adding at least one acid, for example, at least one acid chosen from carboxylic acids such as citric acid.

The compositions disclosed herein may further comprise at least one viscosity regulator such as electrolytes and thickeners (associative and nonassociative thickeners). For example, the at least one viscosity regulator may be chosen from sodium chloride, sodium xylenesulfonate, scieroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked polyacrylic acids and crosslinked acrylic acid/$C_{10}$–$C_{30}$ alkyl acrylate copolymers. The at least one viscosity regulator used in the compositions disclosed herein may be present in an amount up to 10% by weight, relative to the total weight of the composition.

The compositions disclosed herein may further comprise up to 5% of at least one of nacreous agents and opacifiers that are well known in the prior art, such as, for example, $C_{16}$ higher fatty alcohols, fatty-chain acyl derivatives such as ethylene glycol and polyethylene glycol monostearate and distearate, and fatty-chain ethers such as, for example, distearyl ether and 1-(hexadecyloxy)-2-octadecanol.

The compositions disclosed herein may further comprise at least one additive chosen from foam synergists such as $C_{10}$–$C_{18}$ 1,2-alkanediols and fatty alkanolamides derived from $C_8$–$C_{24}$ fatty acid monoethanolamine and diethanolamine, silicone and nonsilicone sunscreens, anionic and nonionic polymers, amphoteric polymers, proteins, protein hydrolyzates, hydroxy acids, vitamins, provitamins such as panthenol, and any other additives conventionally used in cosmetics that do not affect the properties of the compositions disclosed herein.

In one embodiment, the compositions may further comprise at least one additive chosen from vitamins, provitamins and hydroxy acids such as citric acid and tartaric acid.

Needless to say, a person skilled in the art will take care to select this or these optional additional compound(s) and/or the amounts thereof such that the advantageous properties intrinsically associated with the compositions disclosed herein are not, or are not substantially, adversely affected by the envisioned addition(s).

For example, the at least one additive may be present in the compositions disclosed herein in an amount ranging from 0.00001% to 20% by weight, relative to the total weight of the composition. The precise amount of each at least one additive is readily determined by a person skilled in the art depending on its nature and its function.

These compositions may, for example, be in a form chosen from liquids, creams and gels and the compositions may, for example, be suitable for washing and/or caring for a keratin material, for example, the hair and the skin and, further, for example, the hair.

The compositions disclosed herein may, for example, be used for washing and/or treating a keratin material such as the hair, the skin, the eyelashes, the eyebrows, the nails, the lips and the scalp. In one embodiment, the compositions disclosed herein are used for washing and/or treating the hair.

When the compositions disclosed herein are used as standard shampoos, the composition, for example, can be applied to wet hair, the mousse can be generated by massaging and/or friction with the hands, the composition can then be removed, after an optional action time, by rinsing with water, the operation possibly being repeated at least one time.

Further disclosed herein is a process for washing and/or conditioning a keratin material such as, the hair, comprising applying to said wet material an effective amount of a composition as defined above, and rinsing the keratin material with water after an optional action time.

The compositions disclosed herein may, for example, be used as shampoos for washing and/or conditioning the hair, and in this case the composition is applied to the wet hair in amounts that are effective to wash it, this application being followed by rinsing with water.

The compositions disclosed herein may also, for example, be used as shower gels for washing and/or conditioning the hair and/or the skin, in which case the compositions is applied to the wet skin and/or hair and is rinsed off after application.

The compositions disclosed herein may further, for example, be, in a form of washing compositions for the skin, for example, in a form chosen from bath and shower solutions, gels and makeup-removing products.

The cosmetic compositions disclosed herein may, for example, be provided in a form chosen from gels, milks, creams, emulsions, thickened lotions and foams, and may, for example, be used for the skin, the nails, the eyelashes, the lips and the hair. In one embodiment, the cosmetic composition disclosed herein are used on the hair.

The compositions disclosed herein may be packaged in various forms. For example, it may be packaged in a form chosen from vaporizers, pump-dispenser bottles and aerosol containers to apply the composition in vaporized form and in the form of a mousse. Such packaging forms are recommended, for example, when it may be desired to obtain a spray, a lacquer or a mousse for treating the hair.

Concrete, but in no way limiting, examples illustrating the embodiments disclosed herein will now be given.

EXAMPLE 1

A shampoo A in accordance with the embodiments disclosed herein and a shampoo B not in accordance with the disclosed embodiments, having the compositions below, were prepared:

| in g | A | B |
|---|---|---|
| Sodium lauryl ether sulfate (2.2 OE) as an aqueous solution containing 70% AM | 15.4 g AM | 15.4 g AM |
| Cocoylbetaine as an aqueous solution containing 30% AM | 2.4 g AM | 2.4 g AM |
| Inulin from chicory root (fructose/glucose) in powdered form (FIBRULINE from Cosucra) | 0.5 g | — |
| Polydimethylsiloxane (viscosity: 500000 cSt) (MIRASIL DM 500000 from Rhodia) | 1.5 g | 1.5 g |
| Hydroxyethylcellulose quaternized with 2,3-epoxy-propyltrimethylammonium chloride (JR400 from Amerchol) | — | 0.4 |
| 1-(Hexadecyloxy)-2-octadecanol/cetyl alcohol mixture | 2.5 g | 2.5 g |
| Coconut acid monoisopropanolamide | 1 g | 1 g |
| Crosslinked polyacrylic acid CARBOPOL 980 from Noveon | 0.2 g | 0.2 g |
| Fragrance, preserving agent | qs | qs |
| N-Oleoyldihydrosphingosine | 0.01 g | 0.01 g |
| pH = 6.5 ± 0.5 | | |
| Water qs | 100 g | 100 g |

AM = active material

A shampoo wash was performed by applying about 12 g of the composition to premoistened hair. The shampoo was worked into a lather and was then rinsed out thoroughly with water.

The composition had a thick and very fondant texture when applied to wet hair. It showed good rinsability.

A panel of experts found that the compositions in accordance with the embodiments disclosed herein gave the hair, after rinsing, a noteworthy treating effect which was manifested, for example, by an ease of disentangling and of styling, and also noteworthy smoothness and softness of the hair.

Hair washed with composition A was more volumized and was easier to shape than hair treated with composition B. It felt less laden than the hair treated with composition B.

EXAMPLE 2

A shampoo in accordance with the embodiments disclosed herein, having the composition below, was prepared:

| in g | A | B |
|---|---|---|
| Sodium lauryl ether sulfate (2.2 OE) as an aqueous solution containing 70% AM | 11.2 AM g | 11.2 g AM |
| Cocoylamidobetaine/glyceryl monolaurate mixture as an aqueous solution containing 30% AM (TEGOBETAINE HS from Goldschmidt) | 1.92 g AM | 1.92 g AM |
| Inulin from chicory root (fructose/glucose) in powdered form (FIBRULINE from Cosucra) | 0.6 g | — |
| Citric acid | 3 g | 3 g |
| Hydroxyethylcellulose quaternized with 2,3-epoxypropyltrimethylammonium chloride (JR400 from Amerchol) | — | 0.3 |
| Tartaric acid | 0.2 g | 0.2 g |
| Water-glycol extract of green tea leaf (HERBASOL green tea extract from Cosmetochem) | 0.01 g | 0.01 g |
| Water-glycol extract of yellow grapefruit (VEGETOL HYDROGLYCOLIQUE Pamplemousse GR 403 from Gattefosse) | 0.01 g | 0.01 g |
| Fragrance, preserving agent | Qs | qs |
| N-Oleoyldihydrosphingosine | 0.01 g | 0.01 g |
| Aqueous ammonia containing 20.5% NH3, qs pH | 5.3 | 5.3 |
| Water qsp | 100 g | 100 g |

Hair washed with composition A was easy to disentangle and was smooth. It had more volume and was easier to shape than hair treated with composition B. It had a less laden feel than hair treated with composition B.

EXAMPLE 3

A shampoo having the composition below was prepared:

| in g | A | B |
|---|---|---|
| Sodium lauryl ether sulfate (2.2 OE) as an aqueous solution containing 70% AM | 15.4 g AM | 15.4 g AM |
| Cocoylbetaine as an aqueous solution containing 30% AM | 2.4 g AM | 2.4 g AM |
| Potato maltodextrin (MD14 from Avebe) | 1.5 g | — |
| Polydimethylsiloxane (viscosity: 500000 cSt) (MIRASIL DM 500000 from Rhodia) | 1.5 g | 1.5 g |
| Hydroxyethylcellulose quaternized with 2,3-epoxy-propyltrimethylammonium chloride (JR400 from Amerchol) | — | 0.4 |
| 1-(Hexadecyloxy)-2-octadecanol/cetyl alcohol mixture | 2.5 g | 2.5 g |
| Coconut acid monoisopropanolamide | 1 g | 1 g |
| Crosslinked polyacrylic acid CARBOPOL 980 from Noveon | 0.2 g | 0.2 g |
| Fragrance, preserving agent | qs | qs |
| N-Oleoyldihydrosphingosine pH = 6.5 ± 0.5 | 0.01 g | 0.01 g |
| Water qsp | 100 g | 100 g |

Hair washed with composition A was easy to disentangle and was smooth. It had more volume and was easier to shape than hair treated with composition B. It felt less laden than hair treated with composition B.

What is claimed is:

1. A detergent and conditioning composition, comprising, in a cosmetically acceptable medium,
    at least one anionic surfactant,
    at least one other surfactant chosen from amphoteric, cationic and nonionic surfactants, and
    at least one polysaccharide chosen from nonionic and anionic fructans, wherein the weight ratio of the at least one anionic surfactant to the at least one other surfactant is greater than or equal to 1:1.

2. The composition according to claim 1, wherein the at least one anionic surfactant is present in an amount ranging from 2% to 50% by weight, relative to the total weight of the composition.

3. The composition according to claim 2, wherein the at least one anionic surfactant is present an amount ranging from 3% to 30% by weight, relative to the total weight of the composition.

4. The composition according to claim 3, wherein the at least one anionic surfactant is present in an amount ranging from 3% to 20% by weight, relative to the total weight of the composition.

5. The composition according to claim 1, wherein the at least one other surfactant chosen from amphoteric, nonionic and cationic surfactants is present in an amount ranging from 1% to 50% by weight, relative to the total weight of the composition.

6. The composition according to claim 5, wherein the at least one other surfactant chosen from amphoteric, nonionic and cationic surfactants is present in an amount ranging from 1% to 20% by weight, relative to the total weight of the composition.

7. The composition according to claim 6, wherein the at least one other surfactant chosen from amphoteric, nonionic and cationic surfactants is present in an amount ranging from 1% to 10% by weight, relative to the total weight of the composition.

8. The composition according to claim 1, wherein the weight ratio of the at least one anionic surfactant to the at least one other surfactant ranges from 1:1 to 30:1.

9. The composition according to claim 8, wherein the weight ratio of the at least one anionic surfactant to the at least one other surfactant ranges from 2:1 to 20:1.

10. The composition according to claim 9, wherein the weight ratio of the at least one anionic surfactant to the at least one other surfactant ranges from 3:1 to 10:1.

11. The composition according to claim 1, wherein the at least one anionic surfactant is chosen from sodium, triethanolamine and ammonium ($C_{12}$–$C_{14}$)alkyl sulfates; sodium, triethanolamine and ammonium ($C_{12}$–$C_{14}$)alkyl ether sulfates oxyethylenated with 2.2 mol of ethylene oxide; sodium, triethanolamine, and ammonium ($C_{12}$–$C_{14}$)alkylamido sulfates; sodium cocoyl isethionate; and sodium ($C_{14}$–$C_{16}$)-α-olefin sulfonates.

12. The composition according to claim 1, wherein the amphoteric surfactants are chosen from aliphatic secondary and tertiary amine derivatives, wherein the aliphatic radical is chosen from linear and branched chains comprising from 8 to 22 carbon atoms and comprising at least one water-soluble anionic group; ($C_8$–$C_{20}$)alkylbetaines; sulfobetaines; ($C_8$–$C_{20}$)alkylamido($C_1$–$C_6$)alkylbetaines; and ($C_8$–$C_{20}$)alkylamido($C_1$–$C_6$)alkylsulfobetaines.

13. The composition according to claim 1, wherein the at least one polysaccharide is soluble in the composition.

14. The composition according to claim 1, wherein the at least one polysaccharide is water-soluble.

15. The composition according to claim 1, wherein the at least one polysaccharide is an inulin.

16. The composition according to claim 15, wherein the inulin is nonionic.

17. The composition according to claim 1, wherein the at least one polysaccharide is present in an amount ranging from 0.01% to 5% by weight, relative to the total weight of the composition.

18. The composition according to claim 17, wherein the at least one polysaccharide is present in an amount ranging from 0.1% to 5% by weight, relative to the total weight of the composition.

19. The composition according to claim 18, wherein the at least one polysaccharide is present in an amount ranging from 0.2% to 3% by weight, relative to the total weight of the composition.

20. The composition according to claim 1, further comprising at least one conditioner.

21. The composition according to claim 20, wherein the at least one conditioner is chosen from fluoro oils, fluoro waxes, fluoro gums, carboxylic acid esters, silicones, synthetic oils, cationic polymers, mineral, plant and animal oils, plant waxes, ceramides and pseudoceramides.

22. The composition according to claim 21, wherein the at least one conditioner is chosen from cationic polymers and silicones.

23. The composition according to claim 21, wherein the silicones are chosen from at least one of polyalkylsiloxanes, polyarylsiloxanes, polyalkylarylsiloxanes, silicone gums and resins, and polyorganosiloxanes modified with at least one organofunctional group.

24. The composition according to claim 23, wherein:
(a) the polyalkylsiloxanes are chosen from:
   polydimethylsiloxanes comprising trimethylsilyl end groups;
   polydimethylsiloxanes comprising dimethylsilanol end groups; and
   poly($C_1$–$C_{20}$)alkylsiloxanes;
(b) the polyalkylarylsiloxanes are chosen from:
   linear and branched polydimethylmethylphenylsiloxanes and polydimethyldiphenylsiloxanes with a viscosity ranging from $1 \times 10^{-5}$ to $5 \times 10^{-2}$ m²/s at 25° C.;
(c) the silicone gums are chosen from polydiorganosiloxanes with number-average molecular masses ranging from 200 000 to 1 000 000, which are used alone or in the form of a mixture in a solvent; and
(d) the organopolysiloxane resins are chosen from resins comprising units: $R_3SiO_{1/2}$, $R_2SiO_{2/2}$, $RSiO_{3/2}$, $SiO_{4/2}$ wherein R is chosen from hydrocarbon-based groups comprising from 1 to 16 carbon atoms or a phenyl group.

25. The composition according to claim 23, wherein the at least one organofunctional group is chosen from:
a) substituted and unsubstituted amine groups,
b) (per)fluoro groups,
c) thiol groups,
d) carboxylate groups,
e) hydroxylated groups,
f) alkoxylated groups,
g) acyloxyalkyl groups,
h) amphoteric groups,
i) bisulfite groups,
j) hydroxyacylamino groups,
k) carboxylic acid groups,
l) sulfonic groups, and
m) sulfate and thiosulfate groups.

26. The composition according to claim 21, wherein the silicones are chosen from linear polydimethylsiloxanes comprising trimethylsilyl end groups, linear polydimethylsiloxanes comprising hydroxydimethylsilyl end groups, silicone resins, amodimethicones and trimethylsilylamodimethicones.

27. The composition according to claim 21, wherein the synthetic oils are chosen from polyolefins chosen from hydrogenated polybutene, nonhydrogenated polybutene, hydrogenated polydecene, and nonhydrogenated polydecene.

28. The composition according to claim 21, wherein the animal and plant oils are chosen from sunflower oil, maize oil, soybean oil, avocado oil, jojoba oil, marrow oil, grapeseed oil, sesame oil, hazelnut oil, fish oils, glyceryl tricaprocaprylate, plant and animal oils of formula $R_9COOR_{10}$ wherein $R_9$ is chosen from higher fatty acid residues comprising from 7 to 29 carbon atoms and $R_{10}$ is chosen from linear and branched hydrocarbon-based chains comprising from 3 to 30 carbon atoms.

29. The composition according to claim 28, wherein the plant and animal oils of formula $R_9COOR_{10}$ are chosen from alkyl and alkenyl, natural and synthetic essential oils.

30. The composition according to claim 29, wherein the plant and animal oils of formula $R_9COOR_{10}$ are chosen from eucalyptus oil, lavandin oil, lavender oil, vetiver oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil.

31. The composition according to claim 21, wherein the plant waxes are chosen from carnauba wax, candelilla wax, ozokerite, olive wax, rice wax, hydrogenated jojoba wax, the absolute waxes of flowers, and marine waxes.

32. The composition according to claim 31, wherein the absolute wax of flowers is the essential wax of blackcurrant flower.

33. The composition according to claim 21, wherein the ceramides and pseudoceramides correspond to formula (VIII):

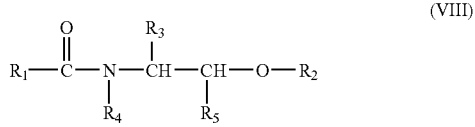

(VIII)

wherein:
$R_1$ is chosen from:
  either: saturated and unsaturated, linear and branched $C_1$–$C_{50}$ hydrocarbon-based radicals, wherein the $C_1$–$C_{50}$ hydrocarbon-based radicals may be substituted with at least one hydroxyl group which may be esterified with an acid $R_7COOH$, wherein $R_7$ is chosen from saturated and unsaturated, linear and branched, $C_1$–$C_{35}$ hydrocarbon-based radicals optionally hydroxylated with at least one hydroxyl group, wherein the at least one hydroxyl group of the radical $R_7$ may be esterified with saturated and unsaturated, linear and branched, optionally mono- and polyhydroxylated $C_1$–$C_{35}$ fatty acids;
  or a radical R"—(NR—CO)—R', wherein R is chosen from a hydrogen atom and mono- and polyhydroxylated $C_1$–$C_{20}$ hydrocarbon-based radicals, R' and R", which may be identical or different, are each chosen from hydrocarbon-based radicals, the sum of the carbon atoms ranging from 9 to 30, and R' is a divalent radical;

or a radical $R_8$—O—CO—$(CH_2)_p$, wherein $R_8$ is chosen from $C_1$–$C_{20}$ hydrocarbon-based radicals, and p is an integer ranging from 1 to 12;

$R_2$ is chosen from a hydrogen atom, a saccharide radical, sulfate and phosphate residues, a phosphorylethylamine radical and a phosphorylethylammonium radical;

$R_3$ is chosen from a hydrogen atom and saturated and unsaturated $C_1$–$C_{33}$ hydrocarbon-based radicals optionally hydroxylated with at least one hydroxyl group, wherein the at least one hydroxyl group may be esterified with an inorganic acid or an acid $R_7$COOH, wherein $R_7$ has the same meanings as above, wherein the at least one hydroxyl may be etherified with at least one radical chosen from (glycosyl)$_n$, (galactosyl)$_m$, sulfogalactosyl, phosphorylethylamine and phosphorylethylammonium radicals, and wherein $R_3$ may also be substituted with at least one radical chosen from $C_1$–$C_{14}$ alkyl radicals;

$R_4$ is chosen from a hydrogen atom, methyl and ethyl radicals, saturated and unsaturated, linear and branched, optionally hydroxylated $C_3$–$C_{50}$ hydrocarbon-based radicals and a radical —$CH_2$—CHOH—$CH_2$—O—$R_6$ wherein $R_6$ is chosen from $C_{10}$–$C_{26}$ hydrocarbon-based radicals and radical $R_8$—O—CO—$(CH_2)_p$, wherein $R_8$ is chosen from $C_1$–$C_{20}$ hydrocarbon-based radicals, and p is an integer ranging from 1 to 12;

$R_5$ is chosen from a hydrogen atom and saturated and unsaturated, linear and branched, $C_1$–$C_{30}$ hydrocarbon-based radicals optionally hydroxylated with at least one hydroxyl group, wherein the at least one hydroxyl may be etherified with at least one radical chosen from (glycosyl)$_n$, (galactosyl)$_m$, sulfogalactosyl, phosphorylethylamine and phosphorylethylammonium radicals, with the proviso that when $R_3$ and $R_5$ are both a hydrogen atom or when $R_3$ is a hydrogen atom and $R_5$ is a methyl radical, then $R_4$ is not a hydrogen atom, a methyl radical, or an ethyl radical.

34. The composition according to claim 33, wherein $R_1$ is chosen from $C_5$–$C_{50}$ hydrocarbon-based radicals.

35. The composition according to claim 33, wherein R is chosen from monohydroxylated $C_1C_{20}$ hydrocarbon-based radicals.

36. The compositon according to claim 33, wherein the saccharide radical of $R_2$ is chosen from (glycosyl)$_n$, (galactosyl)$_m$ and sulfogalactosyl radicals, wherein n is an integer ranging from 1 to 4 and m is an integer ranging from 1 to 8.

37. The composition according to claim 33, wherein $R_3$ is chosen from $C_{15}$–$C_{26}$ α-hydroxyalkyl radicals, wherein the hydroxyl group is optionally esterified with at least one acid chosen from $C_{16}$–$C_{30}$ α-hydroxy acids.

38. The composition according to claim 21, wherein the ceramides are chosen from at least one of:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol,
2-N-palmitoylaminohexadecane-1,3-diol,
bis(N-hydroxyethyl-N-cetyl )malonamide,
N-(2-hydroxyethyl)-N-(3-cetyloxy-2-hydroxypropyl) cetylamide, and
N-docosanoyl-N-methyl-D-glucamine.

39. The composition according to claim 20, wherein the at least one conditioner is present in an amount ranging from 0.0001% to 20% by weight, relative to the total weight of the composition.

40. The composition according to claim 39, wherein the at least one conditioner is present in an amount ranging from 0.001% to 10% by weight, relative to the total weight of the composition.

41. The composition according to claim 40, wherein the at least one conditioner is present in an amount ranging from 0.005% to 5% by weight, relative to the total weight of the composition.

42. The composition according to claim 41, wherein the at least one conditioner is present in an amount ranging from 0.005% to 3% by weight, relative to the total weight of the composition.

43. The composition according to claim 42, wherein the at least one conditioner is present in an amount ranging from 0.01% to 3% by weight, relative to the total weight of the composition.

44. The composition according to claim 1, further comprising at least one cationic polymer.

45. The composition according to claim 44, wherein the at least one cationic polymer is chosen from quaternary cellulose ether derivatives, cationic cyclopolymers, cationic polysaccharides and quaternary polymers of vinylpyrrolidone and of vinylimidazole.

46. The composition according to claim 45, wherein the cationic cyclopolymers are chosen from diallyldimethylammonium chloride homopolymers and copolymers of diallyldimethylammonium chloride and of acrylamide.

47. The composition according to claim 45, wherein the quaternary cellulose ether derivatives are chosen from hydroxyethylcelluloses that have reacted with an epoxide substituted with at least one trimethylammonium group.

48. The composition according to claim 45, wherein the cationic polysaccharides are chosen from guar gums modified with a 2,3-epoxypropyltrimethylammonium salt.

49. The composition according to claim 44, wherein the at least one cationic polymer is present in an amount ranging from 0.001% to 10% by weight, relative to the total weight of the composition.

50. The composition according to claim 49, wherein the at least one cationic polymer is present in an amount ranging from 0.005% to 5% by weight, relative to the total weight of the composition.

51. The composition according to claim 50, wherein the at least one cationic polymer is present in an amount ranging from 0.01% to 3% by weight, relative to the total weight of the composition.

52. The composition according to claim 1, further comprising at least one additive chosen from foam synergists, silicone and nonsilicone sunscreens, anionic polymers, nonionic polymers, and amphoteric polymers, proteins, protein hydrolyzates, hydroxy acids, vitamins, and provitamins.

53. The composition according to claim 52, wherein the foam synergists are chosen from $C_{10}$–$C_{18}$ 1,2-alkanediols and fatty alkanolamides derived from monoethanolamine and from diethanolamine.

54. The composition according to claim 52, wherein the provitamins are panthenol.

55. The composition according to claim 1, further comprising at least one additive chosen from vitamins, provitamins and hydroxy acids.

56. The composition according to claim 1, wherein said at least one anionic surfactant and said at least one other surfactant are present in the composition in a combined amount greater than or equal to 4% by weight, relative to the total weight of the composition.

57. The composition according to claim 56, wherein said at least one anionic surfactant and said at least one other surfactant are present in the composition in a combined amount ranging from 5% to 60% by weight, relative to the total weight of the composition.

58. The composition according to claim 57, wherein said at least one anionic surfactant and said at least one other surfactant are present in the composition in a combined amount ranging from 5% to 30% by weight, relative to the total weight of the composition.

59. The composition according to claim 58, wherein said at least one anionic surfactant and said at least one other surfactant are present in the composition in a combined amount ranging from 5% to 20% by weight, relative to the total weight of the composition.

60. The composition according to claim 1, wherein the composition is provided in a form chosen from shampoos, compositions for permanent-waving the hair, compositions for relaxing the hair, compositions for dyeing the hair, compositions for bleaching the hair, rinse-out compositions to be applied between the two steps of a permanent-waving or relaxing operation, and washing compositions for the skin.

61. A method for shampooing a keratin material comprising applying to the keratin material a composition comprising, in a cosmetically acceptable medium,
at least one anionic surfactant,
at least one other surfactant chosen from amphoteric, cationic and nonionic surfactants, and
at least one polysaccharide chosen from nonionic and anionic fructans, wherein the weight ratio of the at least one anionic surfactant to the at least one other surfactant is greater than or equal to 1:1.

62. A method for washing and/or conditioning keratin fibers comprising:
applying to wet fibers an effective amount of a composition comprising, in a cosmetically acceptable medium,
at least one anionic surfactant,
at least one other surfactant chosen from amphoteric, cationic and nonionic surfactants, and
at least one polysaccharide chosen from nonionic and anionic fructans, wherein the weight ratio of the at least one anionic surfactant to the at least one other surfactant is greater than or equal to 1:1 and
rinsing the keratin fibers with water after an optional action time.

63. The method according to claim 62, wherein the keratin fibers are hair.

* * * * *

UNITED STATES PATENT AND TRADEMARK OFFICE
CERTIFICATE OF CORRECTION

| | |
|---|---|
| PATENT NO. | : 7,157,413 B2 |
| APPLICATION NO. | : 10/614092 |
| DATED | : January 2, 2007 |
| INVENTOR(S) | : Pascale Lazzeri and Alice Apvrille |

It is certified that error appears in the above-identified patent and that said Letters Patent is hereby corrected as shown below:

On the title page, item (54), line 5, "POLYSACCHARDIE," should read --POLYSACCHARIDE,--.

*In claim 3, column 28, line 16, "present an" should read --present in an--.

In claim 35, column 31, line 46, "$C_1C_{20}$" should read --$C_1$-$C_{20}$--.

In claim 38, column 31, line 67, "bis(N-hydroxyethyl-N-cetyl )malonamide," should read --bis(N-hydroxyethyl-N-cetyl)malonamide,--.

Signed and Sealed this

First Day of May, 2007

JON W. DUDAS
*Director of the United States Patent and Trademark Office*